United States Patent [19]

Plapp et al.

[11] Patent Number: 4,841,818

[45] Date of Patent: Jun. 27, 1989

[54] VIAL STOPPER REMOVAL DEVICE

[76] Inventors: Christopher V. Plapp, 8319 Reeds Ln., Overland Park, Kans. 66207; Frederick A. Plapp, 5000 Rock Creek La., Mission, Kans. 66205; Frederick V. Plapp, 8319 Reeds Ln., Overland Park, Kans. 66207

[21] Appl. No.: 150,541

[22] Filed: Feb. 1, 1988

[51] Int. Cl.$^4$ .............................................. B25B 27/00
[52] U.S. Cl. ...................................... 81/3.08; 53/492; 81/3.4; 215/296
[58] Field of Search ........................ 81/3.08, 3.07, 3.4; 53/492, 381 A; 215/296, 306

[56] References Cited

U.S. PATENT DOCUMENTS

| | | | |
|---|---|---|---|
| 4,067,473 | 1/1978 | Awer et al. ...................... | 215/296 X |
| 4,522,089 | 6/1985 | Alvi ...................................... | 81/3.42 |
| 4,726,264 | 2/1988 | Bost ......................................... | 81/3.4 |

Primary Examiner—Donald F. Norton

Attorney, Agent, or Firm—Kokjer, Kircher, Bradley, Wharton, Bowman & Johnson

[57] ABSTRACT

A device and method for removing closures from laboratory sample containers is the subject of the present invention. The device consists of a tubular member which is large enough to contain a laboratory sample container or vial. Integral with one end of the tubular member is a housing member which is large enough to contain the stopper or closure for the laboratory vial and is thus of a diameter larger than the tubular member. The end of the housing opposite the tubular member is closable with an irreversibly locking cap. A vial with a stopper to be removed is placed into the cap end of the housing member and is received by the tubular member unitl the stopper rests on the bottom surface of the housing member. The cap on the housing member is closed and a force is exerted on the vial to dislodge the stopper from it. The vial is pulled through the tubular member, leaving the stopper in the housing member. The open end of the tubular member may then be closed by either a second irreversible locking cap or a flexible resilient skirt.

9 Claims, 1 Drawing Sheet

VIAL STOPPER REMOVAL DEVICE

This invention relates generally to a device and method for removing closures from laboratory containers and, more particularly, to a method and device for removing the stopper from a vial so as to preclude exposure of a worker to the contents and to preclude contamination of the contents by the worker.

In virtually every area of scientific endeavor, glass or plastic tubes are utilized to retain samples for future analysis. Radioactive materials and human and animal blood are among the more common materials which are maintained in vials for a period of time prior to analysis. Vials are typically of circular cross-section, but may also be of polygonal cross-section and constructed of various materials. While plastic and glass are most commonly used, in the case of radioactive materials a vial is constructed of material which will shield workers from the radiation.

In recent years, vacuum vials which are closed with a rubber closure or stopper have been widely used in laboratory medicine. Vacuum tubes can be used in conjunction with a needle holder so that a technician can insert one end of the needle into a vein and the opposite end of the needle is used to puncture the stopper on the vacuum vial. Blood is drawn into the vial by virtue of the partial vacuum thus eliminating the need for a plunger of the type used in a conventional syringe. The technician can then remove one vial and insert another without ever withdrawing the needle from the vein. Vials of the type described are provided with stoppers which are penetrable by a sharp needle but are also self-sealing once the needle is withdrawn.

While vacuum vials are extremely efficient and virtually preclude any contamination of the blood sample by the atmosphere or by a careless technician during sample collection, these vials provide somewhat of a hazard to the analytical technician who removes the stopper prior to undertaking analytical procedures. Because of the vacuum within the vial, when the stopper is removed, a slight aerosol effect may occur which can result in splattering of the worker by the sample contained within the vial or the rapid release of contaminated air which may in and of itself pose a health hazard. Even in the absence of the "aerosol effect", there is always some danger of blood within a vial being spilled or splattered upon a worker during handling of the vial to remove the stopper. Similar hazards potentially exist when a stoppered vial contains radioactive material, tissue samples, urine, saliva, cerebral spinal fluids, amniotic fluids and other body fluids, secretions and excretions, or any one of the large number of other substances which may be retained within a stoppered vial.

Another danger from handling stoppered vials containing potentially hazardous blood samples and other fluids is that, during handling, some of the fluid may be retained in the area of the vial where the stopper engages the sides of the vial. Any fluid in this area is particularly likely to splatter or spill on a technician opening the vial.

Droplets of blood or other fluid are also known to adhere to the end of a rubber stopper used to close a vial and these droplets may contact the skin of a technician during opening of a stoppered vial.

It is also known that, in some instances, fluid contained in the vial may actually spill or leak in the area of the stopper and be dried around the stopper by the time it reaches a laboratory for analysis. Even this dried fluid may pose a threat to a technician handling the vial.

There is also a possibility of a worker who is handling a stoppered vial contaminating the contents of the vial through carelessness or accident during removal of the closure device. The foregoing hazards would be substantially eliminated by a device for safely opening a stoppered vial inside of an enclosure which separates the worker from the contents of the vial.

It is known in the art to utilize a completely mechanical opening device which is maintained within a sterile cabinet in which stoppered vials are placed. This device in effect is a "robot" which mechanically removes the vial closure devices so as to preclude any contamination of the contents by a human and also to eliminate any danger of exposing a human worker to the contents during the unstoppering procedure. These devices are high in cost and are subject to the usual maintenance problems associated with any type of laboratory equipment.

It has also been proposed that a rubber or other non-slip cloth-like cover be placed over the stopper so as to assist in gripping the stopper and also to offer some degree of protection to the person who is opening the vial. Such a device does not offer complete protection against the "aerosol effect", and offers only limited protection against accidental spills and the like.

Another known device for use in removing vial stoppers is in the form of a cap with finger extensions which grasps the stopper and encloses it within the "cap chamber" after which the stopper may be pulled from the vial. This device is relatively expensive, does not offer complete protection from the aerosol effect, offers limited protection against contamination of the sample within the vial, and can be cost justified only if it is to be used a number of times. Repeated use of such a device can pose a hazard to the worker even if no contamination is apparent to the naked eye.

It is, therefore, a primary object of the present invention to provide a method and device for safely opening a vial which may contain a hazardous material by providing an enclosed area which separates the face of a human technician from the end of the vial containing the stopper.

As a corollary to the aforestated object, a primary aim of the invention is to provide a method and device of the type described which can be operated by the least skilled laboratory technician.

Another important objective of this invention is to provide a method and device for safely opening a stoppered vial which may contain hazardous material wherein the stoppered end of the vial is completely enclosed during the opening procedure and yet the device is inexpensive enough to be disposable.

Another objective of our invention is to provide a method and device for safely opening a stoppered vial which includes means for irreversibly closing a safety lid after the vial is placed in the enclosure but prior to removal of the stopper.

It is also an important aim of our invention to provide a method and device for safely opening a stoppered vial which accomplishes the aims and objectives heretofore set forth and which can be made in a variety of sizes and configurations to accommodate vials of both polygonal and round cross-sectional configuration and vials of varying diameters, widths and lengths.

Other objects of the invention will be made clear or become apparent from the following description and claims when read in light of the accompanying drawing:

Figure 1:
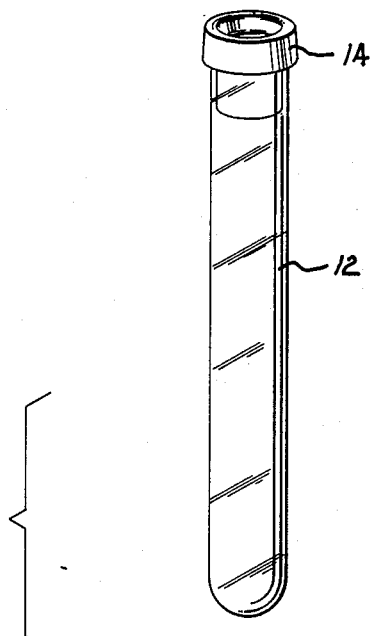
FIG. 1 is a perspective view of a stoppered vial as it would appear just before entering the stopper removal device of the present invention.
Figure 1:
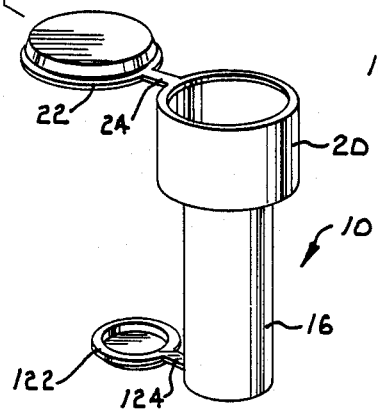

Referring initially to FIG. 1, the device of the present invention is designated generally by the numeral 10 and is shown in position for receiving a vial 12 which is closed by a rubber stopper 14. It is to be understood that the device 10 can be utilized with vials 12 of varying lengths and cross-sectional configurations and dimensions. Most vials are made of plastic or glass, but other materials, such as those which will shield radiation, may also be employed.

Figure 4:
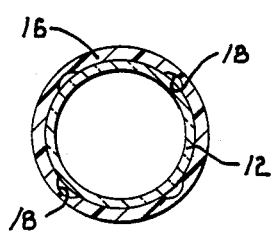
FIG. 4 is a horizontal cross-sectional view taken along line 4—4 of FIG. 2.

Device 10 comprises an elongated tubular member 16 which has an internal cross-sectional dimension that is greater than the external cross-sectional dimension of vial 12 and less than the external cross-sectional dimension of stopper 14. As best illustrated in FIG. 4, a plurality of flutes 18 are disposed in spaced relationship around the inside wall of tubular member 16 and extend the entire length of the tubular member. The terminal end of tubular member 16 is fabricated so as to present an integral peripheral lip 16a for purposes to be made clear hereinafter.

Integral with tubular member 16 is a housing member 20 which is coupled with tubular member 16 at one end so as to provide open communication between members 20 and 16. Housing member 20 has an internal cross-sectional dimension which is large enough to easily accommodate stopper 14 and, accordingly, is larger in internal cross-sectional dimension than the external cross-sectional dimension of the stopper.

It should be noted that the length of housing member 20 is long enough to completely receive stopper 14 within it and the length of tubular member 16 is somewhat less than the length of vial 12 so that the vial will project from the bottom of device 10 when the stopper 14 is resting upon the bottom surface 20a of housing member 20. Housing member 20 also is provided with a horizontally extending lip 20b which projects inwardly a short distance from the inside sidewall of the housing member.

A cap 22 is coupled by hinge 24 to housing member 20 and is provided with a peripheral flange 26 and a cutaway portion 28. Flange 26 tapers as it extends away from the outside of the cap so as to present a reduced diameter section 30 at the innermost cap wall.

The end of tubular member 16 which is opposite housing member 20 is also provided with a cap 122 which is identical in construction to cap 22 described above except that the cap 122 is of smaller diameter so as to close the open end of tubular member 16. A hinge 124 couples cap 122 with tubular member 16. Cap 122 has a peripheral flange 126 and a cutaway portion 128, the same as cap 22, for mating with the peripheral lip 16a and tubular member 16. Again, as with the cap 22, cap 122 has a reduced diameter portion 130 extending below flange 126 so as to facilitate movement of the cap into a locking position as will be discussed hereinafter.

Figure 2:
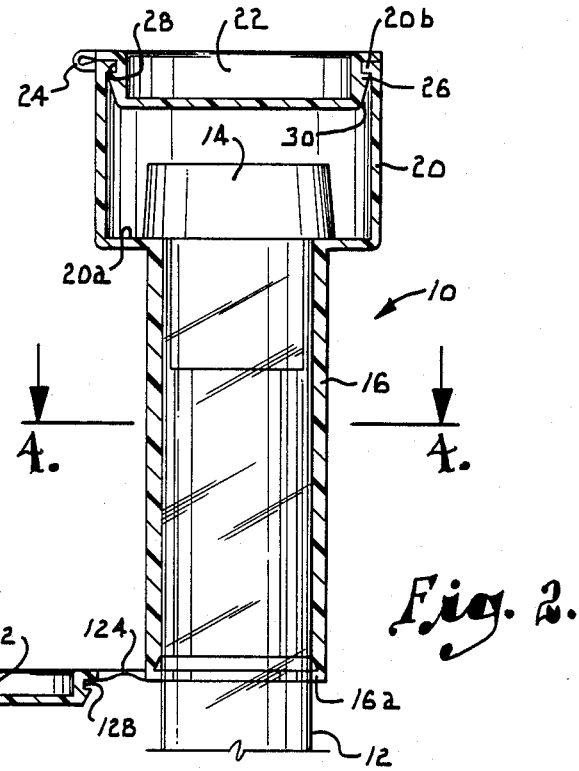
FIG. 2 is a vertical cross-sectional view through the stopper removal device illustrating the stoppered test tube in elevation.

In use, the device 10 is placed in the vial receiving position indicated in FIG. 1 and a vial 12 is inserted into the device by a worker. In this regard, flutes 18 provide an airway passage along the length of tubular member 16 so as to reduce drag between the vial and the tubular member during insertion of the vial. As previously noted, the internal diameter of tubular member 16 is slightly larger than the external diameter of vial 12 so as to easily accommodate movement of the latter through the member. Stopper 14 will come to rest on bottom surface 20a of housing member 20 so as to preclude passage of the stopper through tubular member 16 as illustrated in FIG. 2.

With the vial in place within tubular member 16 and housing member 20, cap 22 is moved to its closed position wherein reduced diameter portion 30 and peripheral flange 26 slide past the peripheral lip 20b so as to bring cutaway portion 28 into engagement with the lip while the top edge of flange 26 engages the underside of the lip. This provides a one way irreversible locking closure for housing member 20 so as to completely enclose stopper 14 within the housing. Vial 12 projects from the lower end of tubular member 16 so as to allow this exposed end to be grasped by a worker who can then exert a force on the vial in a direction away from the stopper so as to dislodge the stopper from the vial. The vial is then withdrawn from the device 10 and stopper 14 remains within. The device 10 with the stopper contained therein may then be discarded utilizing appropriate cautions.

Figure 3:
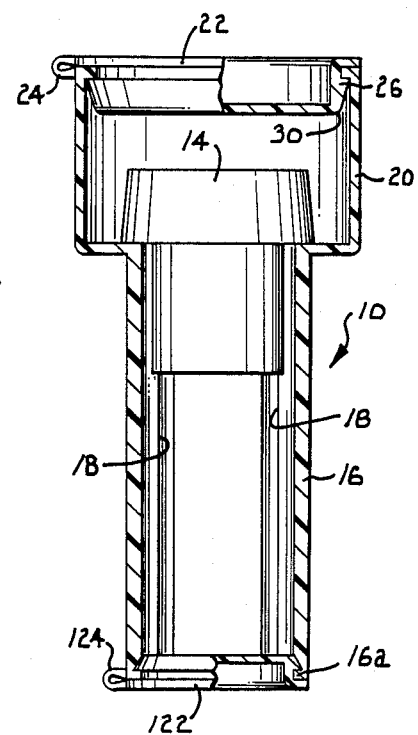
FIG. 3 is another vertical cross-sectional view similar to FIG. 2 after the stopper has been removed and the vial withdrawn from the end of the device.

If additional protection against exposure of a worker to hazardous residuals remaining on stopper 14 is desired, cap 122 may be utilized to close the open end of tubular member 16 immediately upon withdrawal of vial 12. Cap 122 is also irreversibly locked in place once it engages the bottom lip 16a of member 16, as illustrated in FIG. 3. It is also within the scope of the invention to provide a holder on device 10 for a temporary closure device which can be placed over the open end of vial 12 after stopper 14 has been removed. Such a temporary closure device is sometimes employed when different analytical procedures are to be conducted on the same sample and the vial is moved from one piece of analytical equipment to the next within the laboratory.

Figure 5:
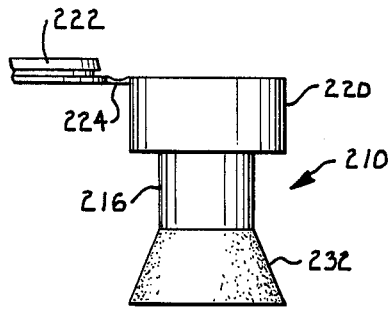
FIG. 5 is a side elevational view of an alternative form of the invention shown in position for accepting a vial.
Figure 6:
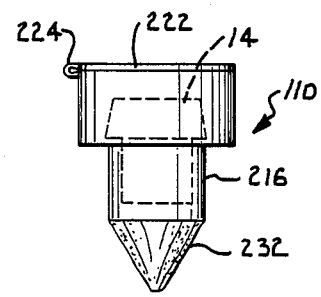
FIG. 6 is an elevational view of the alternative form of the device after a stopper has been removed.

An alternative form of the invention is illustrated in FIGS. 5 and 6 and is designated generally by the numeral 210. Device 210 is provided with a tubular member 216 which is identical to the tubular member 16 previously described for the preferred embodiment except that tubular member 216 is shorter in length. Tubular member 216 is integral with a housing member 220 which is identical to the housing member 20 aforedescribed. Housing member 220 is closed by a cap 222 which is identical to caps 22 and 122 of the preferred embodiment. Cap 222 is joined to housing member 220 by an integrally molded strap hinge 224.

The alternative embodiment 210 differs from the device 10 previously described only in that secured to tubular member 216 is a depending skirt 232 which is made of a flexible, somewhat resilient material. Skirt 232 forms a closure for tubular member 216 thereby eliminating the need for cap 122.

Use of the device 210 is identical to the manner of using the preferred form of the invention previously described, although as the vial 12 is inserted into tubular member 216 skirt 232 will be forced into its open or spread position as illustrated in FIG. 5 so as to allow the vial to pass through the skirt. Cap 222 is closed into its irreversible locking position as illustrated in FIG. 6 and previously described. The vial is then pulled away from the device so as to dislodge stopper 14 which is shown in broken lines in FIG. 6. Once the vial is pulled through tubular member 216, the resilient nature of skirt 232 will cause it to assume the closed or collapsed position illustrated in FIG. 6. Thus, the bottom end of tubular member 216 is automatically closed as the vial is removed without the need to secure a second cap at the bottom end.

It will be appreciated that the present invention has applicability to vials of any shape and configuration, and member 16 will generally be made with a cross-sectional configuration conforming to that of the vial to be opened. It will also be appreciated that the term "stopper" as used herein is intended to encompass any type of vial closure device which could be made of rubber, plastic, cork or other suitable materials with the only criteria being that the external dimension of the stopper be greater than the external dimension of the vial being closed so the stopper presents some type of lip for engagement with the bottom surface of the housing 20 when the vial is inserted within the device of the present invention.

The invention also encompasses a method of removing a stopper from a vial comprising the steps of providing a first open ended enclosure, such as tubular member 16, through which the vial may pass and the stopper will not pass; placing the vial in this first enclosure; and providing a second enclosure which is presented by housing member 20, is coupled with the first enclosure, and is adapted to completely enclose the stopper by virtue of the irreversibly locking cap 22. The next step of the method is to enclose the stopper in this second enclosure while the vial is in the first enclosure followed by the step of exerting a force on the vial in a direction away from the stopper of a sufficient magnitude to dislodge the stopper from the vial.

Other modifications and adaptations of the method and device of the present invention can be made without departing from the scope of the appended claims.

We claim:

1. A device for removing a stopper from a vial, said device comprising:
    an elongated tubular member having a cross-sectional dimension that is greater than the cross-sectional dimension of said vial and less than the cross-sectional dimension of said stopper thereby accommodating movement of said vial through said member while precluding movement of said stopper through said member, said tubular member having a length which is less than the length of said vial;
    a housing member coupled with one end of said tubular member and in open communication with the latter, said housing member having a cross-sectional dimension large enough to accommodate said stopper; and
    first closure means for completely closing the top of said housing member after said stopper is positioned therein,
    whereby when said vial is positioned in said tubular member and said closure means is in place, said vial may be pulled through said tubular member from the end opposite said one end to force said stopper from the vial while substantially precluding exposure of the operator to the contents of said vial.

2. A device as set forth in claim 1, wherein is included means for coupling said first closure means with said housing member.

3. A device as set forth in claim 1, wherein said closure means includes a first locking means and said housing member includes a second locking means adapted to mate with said first locking means when said closure means is in its closing position, said two locking means mating in a manner so as to substantially preclude opening of said closure means after it has assumed its closing position.

4. A device as set forth in claim 3, wherein is included second closure means for closing the end of said tubular member which is opposite said housing member, said second closure means including a first locking means and said tubular member including a second locking means adapted to mate with said first locking means of said tubular member closure means when the latter is in its closing position, said locking means of said tubular member and said second closure means mating in a manner so as to substantially preclude opening of said second closure means after it has assumed its closing position.

5. A device as set forth in claim 4, wherein is included means for coupling said first closure means with said housing member and said second closure means with said tubular member.

6. A device as set forth in claim 1, wherein said tubular member is characterized by a plurality of longitudinally extending internal flutes to accommodate the passage of air while said vial is being moved through said tubular member.

7. A device as set forth in claim 1, wherein said tubular member includes a collapsible skirt which is movable to an open position when said vial is forced through the skirt and is biased into a collapsed position when no opening force is acting on it.

8. A device as set forth in claim 1, wherein is included means for coupling said first closure means with said housing member and wherein said tubular member includes a collapsible skirt which is movable to an open position when said vial is forced through the skirt and is biased into a collapsed position when no opening force is acting on it.

9. A method of removing a stopper from a vial comprising the steps of:
    providing a first open ended enclosure through which said vial may pass and said stopper will not pass;
    placing said vial in said first enclosure;
    providing a second enclosure which is coupled with said first enclosure and is adapted to completely enclose said stopper;
    providing said second enclosure with means for completely closing the top of said second enclosure;
    enclosing said stopper in said second enclosure when said vial is in said first enclosure; and
    exerting a force on said vial in a direction away from said stopper of a sufficient magnitude to dislodge said stopper from said vial.

* * * * *